United States Patent
Wahlstrand et al.

(10) Patent No.: US 8,929,993 B2
(45) Date of Patent: Jan. 6, 2015

(54) ELECTRODE ARRANGEMENTS FOR SUBORBITAL FORAMEN MEDICAL LEAD

(75) Inventors: Carl D. Wahlstrand, North Oaks, MN (US); Dale F. Seeley, Spring Park, MN (US); Lisa M. Johanek, White Bear Lake, MN (US); John E. Kast, Hugo, MN (US); Phillip C. Falkner, Minneapolis, MN (US); Louis P. Vera-Portocarrero, St. Anthony, MN (US)

(73) Assignee: Medtronic, Inc., Minneapolis, MN (US)

( * ) Notice: Subject to any disclaimer, the term of this patent is extended or adjusted under 35 U.S.C. 154(b) by 239 days.

(21) Appl. No.: 13/376,152

(22) PCT Filed: Jun. 21, 2010

(86) PCT No.: PCT/US2010/039297
§ 371 (c)(1),
(2), (4) Date: Dec. 2, 2011

(87) PCT Pub. No.: WO2010/148377
PCT Pub. Date: Dec. 23, 2010

(65) Prior Publication Data
US 2012/0078334 A1  Mar. 29, 2012

Related U.S. Application Data

(60) Provisional application No. 61/218,463, filed on Jun. 19, 2009.

(51) Int. Cl.
*A61N 1/05* (2006.01)

(52) U.S. Cl.
USPC ............................................ 607/53; 607/116

(58) Field of Classification Search
USPC .............. 607/116, 118, 117, 53, 54; 600/377
See application file for complete search history.

(56) References Cited

U.S. PATENT DOCUMENTS

| | | | |
|---|---|---|---|
| 3,804,098 A | 4/1974 | Friedman | |
| 4,774,952 A | 10/1988 | Smits | |
| 5,843,148 A | 12/1998 | Gijsbers | |
| 7,515,968 B2 | 4/2009 | Metzler et al. | |
| 7,672,734 B2 | 3/2010 | Anderson | |
| 7,769,472 B2 | 8/2010 | Gerber | |
| 7,996,092 B2 | 8/2011 | Mrva et al. | |
| 2003/0083716 A1* | 5/2003 | Nicolelis et al. | 607/45 |
| 2004/0117728 A1 | 6/2004 | Gromer | |
| 2007/0191909 A1* | 8/2007 | Ameri et al. | 607/54 |

OTHER PUBLICATIONS

PCT/US10/039294: Search Report and Written Opinion dated Oct. 6, 2010.
PCT/US10/039297: Search Report and Written Opinion dated Oct. 6, 2010.
PCT/US10/039295: Search Report and Written Opinion dated Oct. 11, 2010.

* cited by examiner

*Primary Examiner* — Alyssa M Alter
(74) *Attorney, Agent, or Firm* — Mueting, Raasch & Gebhardt, P.A.

(57) ABSTRACT

A medical lead includes a plurality of electrodes on an annular distal end portion of the lead. The electrodes may be arranged along a circle concentric with the center of a void defined by the annular portion. The annular medical lead design is well suited for application of electrical signal therapy to the suborbital nerve at its point of exit from the inferior orbital foramen in the skull.

21 Claims, 3 Drawing Sheets

ELECTRODE ARRANGEMENTS FOR SUBORBITAL FORAMEN MEDICAL LEAD

RELATED APPLICATION

This application is a U.S. National Stage filing under 35 U.S.C. 371 of copending PCT Application Serial No. PCT/US2010/039297, filed Jun. 21, 2010 which claims the benefit of priority to U.S. provisional patent application No. 61/218,463, filed Jun. 19, 2009, both of which applications are incorporated herein by reference to the extent that they do not conflict with the present disclosure.

FIELD

This disclosure relates to implantable medical devices. More particularly, it relates to implantable medical leads.

BACKGROUND

Many implantable medical devices, such as neurostimulators, pacemakers and defibrillators, transmit electrical signals to provide therapy to a patient. Implantable medical leads deliver signals generated from such devices to tissue of the patient via one or more electrodes of the lead. In some cases, the electrodes are placed adjacent or in contact with a nerve of the patient. Such placement ensures that the generated electrical signals are applied to the intended nerve.

However, placement of the lead in contact with or adjacent to a nerve can result in undesired impingement of the nerve, particularly with more superficial peripheral nerves where little space between the implanted lead and the nerve is available. Lead designs that can allow close placement of a lead to a nerve so that electrical signals emitted from lead can capture the desired nerve without creating a lot of physical pressure on the nerve would be beneficial.

SUMMARY

The present disclosure describes, among other things, various medical leads that may be placed in close proximity to peripheral nerves to facilitate capturing of the nerve by electrical signals emitted from the lead, while reducing the physical impact of the lead on the nerve. In various embodiments, a lead has an annular distal body with a central void. Electrodes are disposed along the annular body. The annular arrangement of electrodes allows electrode selection to ensure capture of a desired nerve, while the central void minimizes the surface area of the lead that may impinge on, or apply pressure to, the nerve.

In various embodiments, an implantable medical lead includes a generally planar annular distal body portion defining a central void, and a plurality of electrodes disposed along the annular distal body portion. The electrodes may be arranged along a path concentric with the center of the central void. In some embodiments the electrodes are evenly spaced. The annular distal body portion may have an outer periphery that is circular or essentially circular, or not circular or essentially circular. The central void may be the same shape or a different shape from the annular distal body portion. In some embodiments, a web is disposed across the central void. The web may have a bending stiffness that is ten times or more less than the bending stiffness of the annular body portion.

The leads described herein may be used to apply electrical signals to a suborbital nerve by placement of the annular body portion in proximity to the suborbital nerve as it exits the suborbital foramen and applying electrical signals to the nerve via the electrodes of the leads. In some embodiments, the central void of the lead is centered with the suborbital foramen as the lead is implanted to enhance the chance that the lead will be placed to capture the suborbital nerve as it exits the foramen.

These and various other features and advantages will be apparent from a reading of the following detailed description.

Figure 1:
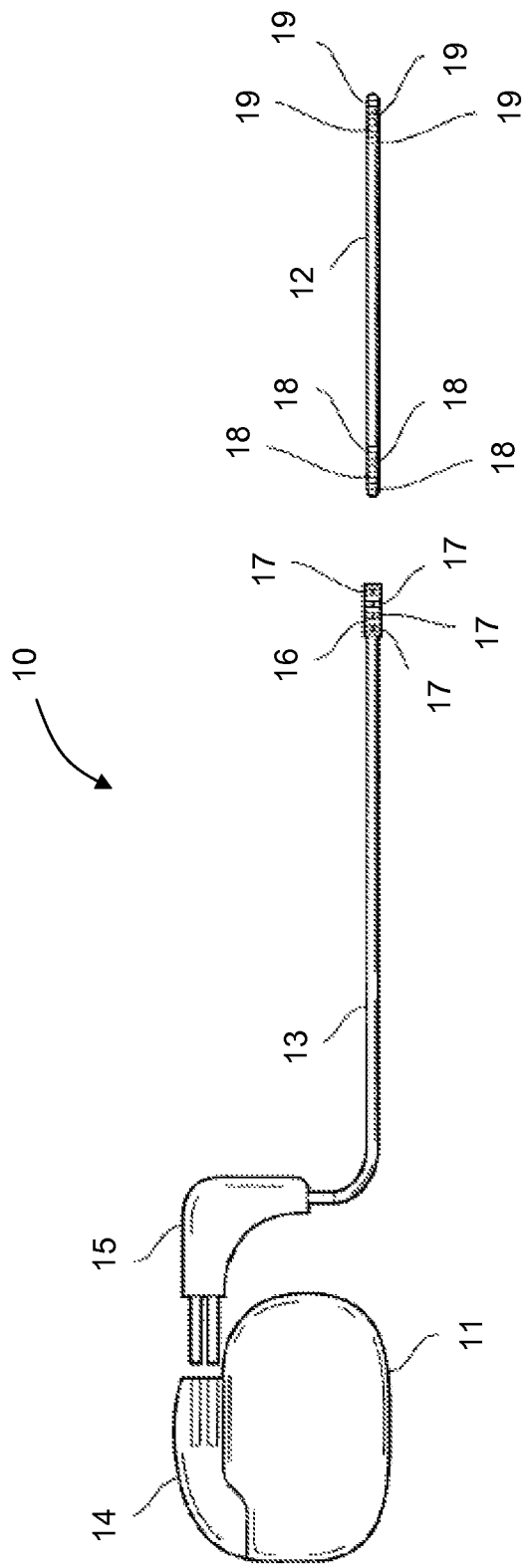
FIG. 1 is a schematic drawing of a representative implantable medical system, illustrating a generic lead.

The drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

In the following detailed description, reference is made to the accompanying drawings that form a part hereof, and in which are shown by way of illustration several specific embodiments of devices, systems and methods. It is to be understood that other embodiments are contemplated and may be made without departing from the scope or spirit of the apparatuses, systems and methods described herein. The following detailed description, therefore, is not to be taken in a limiting sense.

All scientific and technical terms used herein have meanings commonly used in the art unless otherwise specified. Any definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise.

As used herein, "representative" and "exemplary" are used in the context of "providing an example" and do not necessarily indicate that the example provided is superior to, or more particularly suited for the intended purpose than, other potential examples.

Directional terms, such as "longitudinal", "lateral", "transverse", and the like, when used with regard to a lead, are intended to have approximate practical meanings in view of the limp nature of leads (e.g., leads are generally "limp" and are often not in their elongated straight configuration) and the environment of use, rather than precise geometrical meanings.

As used herein, "annular" means shaped like a ring. That is, a structure having a central void is annular. Annular structures, for the purposes of the present disclosure, may, but need not, be generally circular. Annular structures may be oval or elliptical, rectangular, or the like, provided that they have a central void.

The present disclosure describes, among other things, medical leads having an annular distal body with a central void. Electrodes are disposed along the annular body. The annular arrangement of electrodes allows electrode selection to ensure capture of a desired nerve, while the central void minimizes the surface area of the lead that may impinge on, or apply pressure to, the nerve.

The leads presented herein may be used with any suitable implantable electrical medical system. While the disclosure presented herein is directed mainly to use of such leads for applying electrical stimulation therapy to peripheral nerves, it will be understood that the leads described herein may be used for applying electrical signals to tissues other than peripheral nerves or for transmitting signals from a tissue to an electrical medical device for purposes of sensing, monitoring, or the like. When used for purposes of applying electrical signal therapy, leads may be used in conjunction with an electrical signal generator.

Any suitable electrical signal generator system may be employed for applying electrical signals in such a manner. For example and referring to FIG. 1, a side view of an embodiment of a representative system 10 is shown. System 10 includes an implantable electrical signal generator 11, a lead extension 13 and a lead 12. Implantable electrical signal generator 11 includes a connector header 14 configured to receive plug 15 at proximal end of lead extension 13 or other adaptor to operably couple lead 12 to electrical signal generator 11. The distal end portion of lead extension 13 includes a connector 16 configured to receive proximal end portion of lead 12. Connector 16 includes electrical contacts 17 configured to electrically couple extension 13 to lead 12 via electrical contacts 18 on the proximal end portion of lead 12. Electrodes 19 are present on distal end portion of lead 12 and are electrically coupled to electrical contacts 18, typically through conductors (not shown) within lead 12. In general, lead 12 may include any number of electrodes 19, e.g. one, two, three, four, five, six, seven, eight, sixteen or any other number. In some embodiments, each electrode 19 is electrically coupled to a discrete electrical contact 18, whereas in other embodiments, a set of electrodes 19 is electrically coupled to a discrete contact 18. While not shown, it will be understood that more than one lead 12 may be operably coupled to one electrical signal generator 11 or one extension 13 or that more than one extension 13 may be operably coupled to one electrical signal generator 11. It will be further understood that lead 12 may be coupled to electrical signal generator 11 without use of extension 13 or other adaptor.

Figure 2:
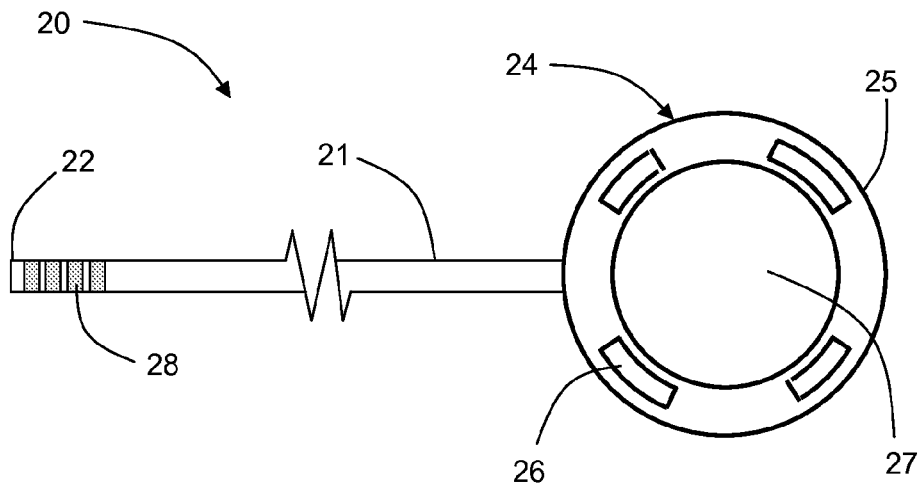
FIGS. 2-4 are a schematic side view of embodiments of leads.
Figure 3:
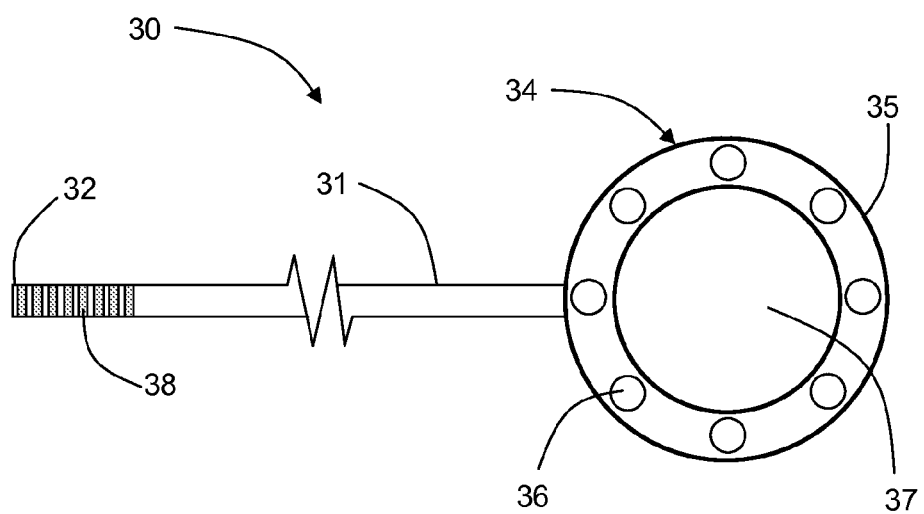
Figure 4:
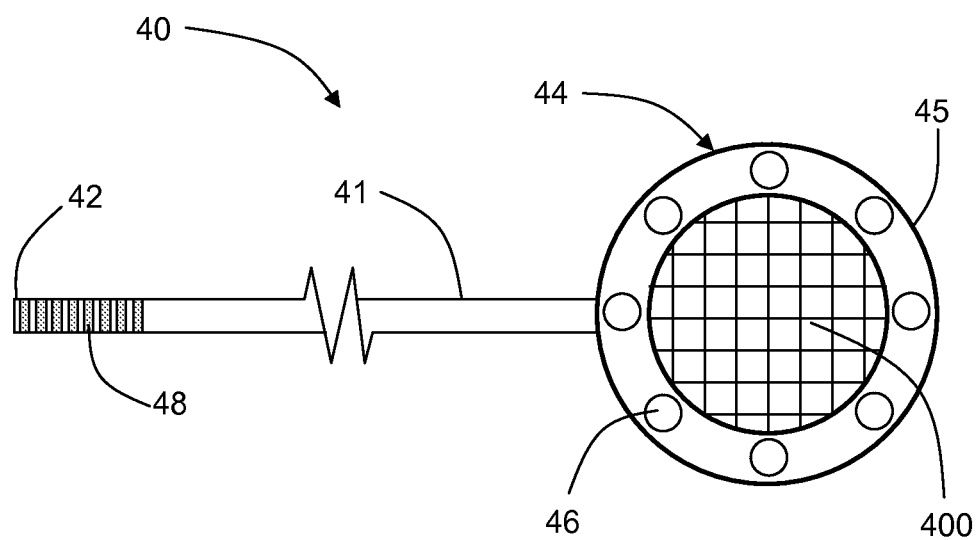

Among other things, the present disclosure is directed to various embodiments of leads 12 having an annular distal body with various arrangements of electrodes 19 on the distal portion. The annular body with a central void allows for the electrodes, in some embodiments, to be placed in close proximity to a nerve while limiting the pressure placed on the nerve by the distal end of the lead. FIGS. 2-4 illustrate embodiments of leads having an annular distal body portion having a plurality of electrodes on the annular portion that can be used as part of system 10.

Referring to FIG. 2, a lead 20 is illustrated having a lead body 21 with a proximal end 22 and a distal end portion 24 having a generally flat or planar annular region 25 defining a central void 27. Present on annular region 25 of distal end body portion 24 are a plurality of electrodes 26. In the depicted embodiment, the electrodes 26 are radially or concentrically positioned with regard to the central void 27. That is, the centers of the electrodes 26 are equidistant to the center of the central void 27. Due to the lack of a lead body, the central void 27 is free of electrodes.

In the embodiment in FIG. 2, lead 20 has four electrodes 26 on annular body region 25, each generally rectangular in shape with a curvature following annular region 25. Two opposing electrodes 26 have a larger surface area than the other two electrodes 26. Each electrode 26 is separately electrically connected to a contact 28 at proximal end 22 of lead 20. In alternate embodiments, multiple electrodes can be electrically coupled to the same electrode contact.

Similar to lead 20 of FIG. 2, a lead 30 is illustrated in FIG. 3 having a lead body 31 with a proximal end 32 and a distal end portion 34 having a generally flat or planar annular body region 35 defining a central void 37. Present on the distal annular body portion 35 are a plurality of electrodes 36 radially or concentrically positioned with regard to the central void 37. In this embodiment, lead 30 has eight electrodes 36 evenly spaced on annular body region 35, each generally circular in shape. Each electrode 36 is discretely electrically connected to a contact 38 positioned at proximal end 32 of lead 30. In alternate embodiments, multiple electrodes can be electrically coupled to the same electrode contact.

Leads described herein may be of any suitable size. In many embodiments, a lead has a diameter of about 5 mm or less; e.g., about 1.5 mm or less, along the proximal body portion. In some embodiments, the distal end portion 24, 34 having an annular body 25, 35, in its unstressed, natural state, has an outer diameter of about 10 mm (1 cm) or less; e.g., about 5 mm or less or about 4 mm or less. The distal end portion 24, 34 having an annular body 25, 35 may have any suitable thickness, such as about 3 mm or less or about 1 mm or less. In many embodiments, the central void 27, 37 has a diameter that is at least about 1 mm less than the diameter of distal end portion (and of annular region 25, 35), such as about 2 mm less that the diameter of distal end portion 24, 34. Central void 27, 37, in many embodiments, is centered in distal end portion 24, 34, so that annular body region 25, 35 has a constant width around.

It is noted that although distal end portion 24, 34 are illustrated as being circular, it is understood that in some embodiments, distal end portion 24, 34 may have a different shape, such as essentially or nearly circular (e.g., having a radius varying no more than 10% around the shape), elliptical or oval, octagonal, hexagonal, pentagonal, etc. Central void 27, 37 may have the same shape as distal end portion 24, 34, or may be different.

The lead body 21, 31 including the annular body 25, 35 of distal portion 24, 34 may be formed of any suitable material, such as polyurethane. Of course other materials such as silicone may be used. Electrical conductors extending between the proximal end and the distal end portions for supplying electrical current to the electrodes may be formed of any suitable material, such as coiled, braided or stranded wires comprising an electrical conductive material, e.g., MP35N or a platinum-iridium alloy. Electrodes 26, 36 may be formed of any suitable material, such as platinum. Of course other metals and metal alloys, such as gold or stainless steel, can be used. In some embodiments, non-metallic yet electrically conductive materials may be used as the electrodes and/or electrical conductors.

The exposed surface area of electrodes 26, 36 may be any shape, although in most embodiments the electrodes are circular. Other suitable shapes for electrodes include rectangular electrodes, oval or ellipsoid electrodes, and other polygonal shaped electrodes. Electrodes 26, 36 may be arcs or segments of a circle. Multiple electrodes 26, 36 on a medical lead need not all have the same surface area shape or size. The electrodes may be concentrically positioned (i.e., each electrode 26, 36 is the same distance from the center of central void 27, 37) or the electrodes may be staggered in distance from the center of central void 27, 37. The electrodes 26, 36 may have any suitable active surface area, such as about 1 mm² to about 100 mm² (1 cm²) or about 5 mm² to about 20 mm².

Inter-electrode distances are often about 3 mm, but other inter-electrode distances may be used such as about 1 mm, about 2 mm, about 4 mm, about 5 mm, about 6 mm, about 7 mm, about 8 mm, about 9 mm, about 10 mm, about 12 mm, about 14 mm, about 16 mm, about 18 mm, about 20 mm, about 25 mm, and about 30 mm.

In the embodiments depicted in FIGS. 2-3, the central void 27, 37 defined by the annular body portion 25, 35 is void of any and all material; that is, central void 27, 37 is an aperture defined by annular region 25. When implanted, tissue in-growth into the central void 27, 37 may occur. Such in-growth can serve to anchor the distal portion 24, 34 of the lead to prevent lead migration. However, such in-growth may make it more difficult to remove the lead from the patient, should lead removal become necessary or desirable.

In some embodiments and with reference to FIG. 4, a web 400, film, or the like may be disposed across the central void of the annual body portion 45. For the purposes of this disclosure, web, film, membrane, and the line are used synonymously. The web 400 may serve to prevent tissue in-growth into the central void when the lead 40 is implanted, allowing the lead to be more easily removed. The web 400 may be made of any suitable material, such as silicone. In various embodiments, the bending stiffness of the web 400 is ten times or more less (e.g., 20 times or more less) than the bending stiffness of annular body portion 45. By having such a low bending stiffness, the web 400, if placed in contact with, or in close proximity to, a nerve will not impart a great deal of physical stress or pressure on the nerve.

Leads having annular distal body portions as described herein may be used for any suitable purpose. One suitable use of such leads is the treatment of chronic atypical facial pain. A patient with atypical facial pain typically presents with a burning, aching or cramping sensation, typically on one side of the face. The facial pain tends to be continuous with few, if any, periods of remission. While not intending to be bound by theory, it is believed that, at least some patients, atypical facial pain is an early form of trigeminal neuralgia.

Other suitable uses of such leads include the treatment of pain resulting from direct injury to a suborbital (or other) nerve resulting from, for example, facial injuries or facial, plastic or reconstructive surgery; pain resulting from other branches of the maxillary nerve resulting from, for example, oral surgery; and treatment of other pain such as headache, including migraine.

Figure 5:
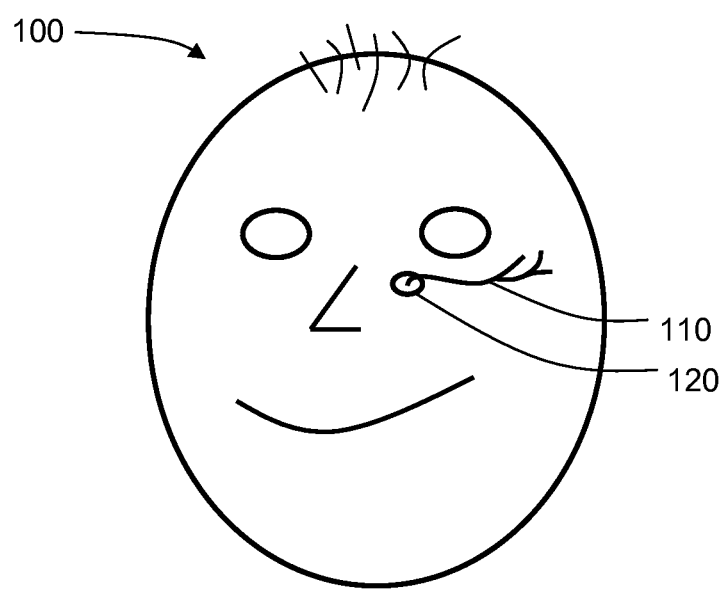
FIG. 5 is a schematic rendition of a patient.

FIG. 5 illustrates a patient 100 in which lead 20, 30 or other variations thereof may be used to treat atypical facial pain or trigeminal neuralgia. Patient 100 is a human, but it is conceivable for the patient to be non-human (e.g., primate, canine, feline, equine, etc.). Patient 100 has a suborbital nerve 110 situated on or below the floor of the orbit of the eye, generally proximate the suborbital cavity or the suborbital zygomatic region. In some situations, suborbital nerve 110 may be referred to as the infraorbital nerve. Nerve 110 exits from the skull through a foramen 120. Lead 20, 30, 40 and other leads having an annular region 25, 35, 45 are well suited for applying electrical signals to nerve 110 proximate foramen 120. Foramen 120 can be readily located with medical imaging, such as with ultrasonics or ultrasound. Similarly, the annular body portion 25, 35, 45 can be readily identified so that the central void 27, 37 or web 400 may be centered on foramen 120. In some embodiments, the annular body portion includes markers, such as radiopaque markers, that make it easier to visualize the annular body portion 25, 35, 45 when using various visualization techniques during the implant procedure. Once properly positioned; e.g. when the central void 27, 37 or web 400 is centered on foramen 120, the proper electrodes 26, 36, 46 can be selected to apply the electrical signal therapy to nerve 110. Thus, the patient 100's facial pain may be treated.

The leads 20, 30, 40 described herein and other leads having an annular distal body portion 25, 35, 45 may be implanted into the patient either in an unstressed, natural state (i.e., with annular region essentially flat and planar) or may be manipulated to a different shape during implantation and then returned to its unstressed state after positioning on foramen 120. For example, distal end portion 24, 34, 44 may be curled or wrapped into a lumen or other carrier to allow insertion via a small introducer. The annular shape of distal end portion 24, 34, 44 facilitates the reduction in shape and size of distal end portion 24, 34, 44, due to the presence of central void 27, 37. Central void 27, 37 increases the flexibility and shapability of distal end region 24, 34, 44 by providing the region free of material. Upon proper positioning of distal end portion 24, 34, 44 at foramen 120, annular region 25, 35 can be returned to its generally flat and planar form. Flexible shape-retaining polymeric materials are particularly suited for distal end portion 24, 34, 44.

Further, the flexible distal end portions 24, 34, 44 have the additional benefit of imparting a reduced amount or stress or pressure to the nerve (relative to less flexible structures) when implanted in close proximity to, or in contact with, a nerve, such as nerve 110.

It will be understood that electrical signal parameters may be varied as desired for treating pain. Typically, the frequency, amplitude or pulse width of an electrical signal may be varied. An electrical signal having any suitable frequency for treating pain may be used to treat pain as described herein. For example, an electrical signal may have a frequency of about 0.5 Hz to 500 Hz (e.g., about 5 Hz to 250 Hz or about 10 Hz to 50 Hz). For example, the amplitude may be about 0.1 volts to 50 volts (e.g., about 0.5 volts to 20 volts or about 1 volt to 10 volts); for devices that the amps rather than voltage, one skilled in electronics understands the conversion from volts to amps for stimulation devices. An electrical signal may have any suitable pulse width. For example, the signal may have a pulse width of 10 microseconds to 5000 microseconds (e.g., about 100 microseconds to 1000 microseconds or about 180 microseconds to 450 microseconds). For some patients 100 with some devices 10, the determination of the optimal location and parameters for stimulation occurs within days, for others, within hours or minutes.

One of skill in the art will understand that components described herein regarding a given embodiment or set of embodiments may readily be omitted, substituted, or added from, with, or to components of other embodiments or sets of embodiments, as appropriate or desirable.

Thus, embodiments of ELECTRODE ARRANGEMENTS FOR SUBORBITAL FORAMEN MEDICAL LEAD are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:
1. An implantable medical lead comprising:
   an annular distal body portion defining a central void, wherein the annular distal body portion in an unstressed state and the central void are generally flat and planar and lie in a plane, wherein an axis passes through a center of the annular distal body portion, intersecting the central void, and wherein the axis is perpendicular to the plane within which the annular distal body portion lies; and a plurality of electrodes disposed along the annular distal body portion wherein the annular distal body portion of the lead is configured to be positioned proximate the infraorbital foramen to treat facial pain by applying an electrical signal via one or more of the plurality of the electrodes.

2. A medical lead according to claim 1, wherein the plurality of electrodes are arranged along a path concentric with the center of the central void.

3. A medical lead according to claim 1, comprising at least four electrodes.

4. A medical lead according to claim 1, wherein the electrodes are evenly spaced.

5. A medical lead according to claim 1, wherein the annular distal body portion has an outer periphery that is circular or essentially circular.

6. A medical lead according to claim 1, wherein the annular distal body portion has an outer periphery that is not circular or essentially circular.

7. A medical lead according to claim 1, wherein the central void region is circular or essentially circular.

8. A medical lead according to claim 1, wherein the annular distal body portion has an outer periphery that is the same shape as the central void region.

9. A medical lead according to claim 1, wherein the annular distal body portion has an outer diameter of 10 mm or less.

10. A medical lead according to claim 1 wherein the annular distal body portion has a diameter of 5 mm or less.

11. A medical lead according to claim 1 wherein the annular distal body portion has a diameter of 4 mm or less.

12. A medical lead according to claim 1, further comprising a web disposed across the central void.

13. A medical lead according to claim 12, wherein the annular distal body portion has a bending stiffness of ten times or more than the bending stiffness of the web.

14. A medical lead according to claim 1, wherein the lead is configured to apply an electrical signal via one or more of the plurality of electrodes to an infraorbital nerve to treat atypical facial pain when the central void is centered with a foramen of the infraorbital nerve.

15. The medical lead according to claim 1, wherein the annular distal body portion defines a first planar surface parallel to the plane that the annular distal body portion lies within, and a second planar surface opposite a the first planar surface, wherein the distance from the first planar surface to the second planar surface defines a thickness, wherein the thickness is less than 3 mm.

16. The medical lead according to claim 1, wherein the annular distal body portion defines a first planar surface parallel to the plane that the annular distal body portion lies within, and a second planar surface opposite a the first planar surface, wherein the distance from the first planar surface to the second planar surface defines a thickness, wherein the thickness is less than 1 mm.

17. The medical lead according to claim 1, wherein the electrodes are equidistant from the center of the annular distal body portion.

18. The medical lead according to claim 1, wherein the central void is free of electrodes.

19. The medical lead according to claim 1, wherein the annular distal body portion completely surrounds the central void.

20. A method for treating facial pain, in a subject in need thereof, comprising:

providing an implantable medical lead having (i) an annular distal body portion defining a central void, wherein the annular distal body portion in an unstressed state and the central void are generally flat and planar and lie in a plane, wherein an axis passes through a center of the annular distal body portion, intersecting the central void, and wherein the axis is perpendicular to the plane within which the annular distal body portion lies; and (ii) a plurality of electrodes disposed along the annular distal body portion;

positioning the annular distal body portion proximate an infraorbital nerve of the subject; and applying an electrical signal via one or more of the electrodes of the lead.

21. A method for treating atypical facial pain, in a subject in need thereof, comprising:

providing an implantable medical lead having (i) an annular distal body portion defining a central void, wherein the annular distal body portion in an unstressed state and the central void are generally flat and planar and lie in a plane, wherein an axis passes through a center of the annular distal body portion, intersecting the central void, and wherein the axis is perpendicular to the plane within which the annular distal body portion lies; and (ii) a plurality of electrodes disposed along the annular distal body portion;

implanting the lead in the subject such that the central void of the lead is centered with a foramen of the infraorbital nerve; and applying an electrical signal to the infraorbital nerve via one or more of the electrodes of the lead.

\* \* \* \* \*